US007381566B2

(12) United States Patent
Terech

(10) Patent No.: US 7,381,566 B2
(45) Date of Patent: Jun. 3, 2008

(54) METHOD FOR PREPARING ORGANIC NANOTUBULES OF LITHOCHOLIC ACID, NANOTUBULES DERIVED THEREFROM, AND USES THEREOF

(75) Inventor: Pierre Terech, Saint-Cassien (FR)

(73) Assignees: Commissariat a l'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 10/483,280

(22) PCT Filed: Jun. 21, 2002

(86) PCT No.: PCT/FR02/02166

§ 371 (c)(1),
(2), (4) Date: Jan. 9, 2004

(87) PCT Pub. No.: WO03/007323

PCT Pub. Date: Jan. 23, 2003

(65) Prior Publication Data

US 2004/0171188 A1    Sep. 2, 2004

(30) Foreign Application Priority Data

Jul. 12, 2001    (FR) .................................. 01 09299

(51) Int. Cl.
*G01N 33/92*    (2006.01)
*C07D 215/04*    (2006.01)
*C07J 9/00*    (2006.01)

(52) U.S. Cl. ........................... 436/71; 540/2; 552/552; 977/734; 977/742; 977/746

(58) Field of Classification Search ................ 977/742, 977/746, 783, 734; 436/71; 540/2; 552/552
See application file for complete search history.

(56) References Cited

U.S. PATENT DOCUMENTS 2,566,342 A * 9/1951 Levin et al. ................ 552/550

(Continued)

FOREIGN PATENT DOCUMENTS

JP        11-246551        9/1999

OTHER PUBLICATIONS

Dennis T. Bong, et al., "Organic Nanotubes", Angewandte Chemie, vol. 40, No. 6, pp. 988-1011 2001.

(Continued)

*Primary Examiner*—Long V. Le
*Assistant Examiner*—Shafiqul Haq
(74) *Attorney, Agent, or Firm*—Oblon, Spivak, McClelland, Maier & Neustadt, P.C.

(57) ABSTRACT

A method for preparing organic nanotubules in an aqueous medium including preparing a basic solution with a pH from 10 to 14, adding an organic compound of the formula:

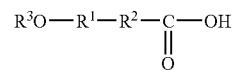

wherein $R^1$ is a $C_{17}$-$C_{20}$ polycyclic radical with fused rings optionally including alkyl substituents, $R^2$ is a $C_3$-$C_{20}$ linear or branched alkylene group, and $R^3$ represents a hydrogen atom, a $C_1$-$C_{20}$ alkyl or $C_6$-$C_{30}$ aromatic group, and submitting the solution to stirring for sufficient time in order to form stable tubules of the organic compound in the solution; and nanotubules prepared by the method.

9 Claims, 2 Drawing Sheets

U.S. PATENT DOCUMENTS 5,649,537 A * 7/1997 Anelli et al. ............... 424/9.3

OTHER PUBLICATIONS

Joel M. Schnur, et al., "Self-assembling phospholipid tubules", Advanced Materials, vol. 6, No. 12, pp. 971-974 Dec. 1, 1994.

Joel M. Schnur, "Lipid tubules: a paradigm for molecularly engineered structures", vol. 262, No. 5140, pp. 1669-1676 Dec. 10, 1993.

M. Trau, et al. Nature, vol. 390, pp. 674-476 Dec. 18-25, 1997.

Cornelus F. van Norstrum, Adv. Mater, vol. 8, No. 12, pp. 1027-1030 1996.

Cees Dekker, "Carbon nanotubes as molecular quantum wires", Physics Today, pp. 22-28 1999.

Jong Hwa Jung, et al., "Sol-gel transcription of novel sugar-based superstructures composed of sugar-integrated gelators into silica: creation of lotus-shaped silica structure", Chem. Commun. pp. 2343-2344 2000.

Weiqiang Gu, et al., "Polymerized gels and 'reverse aerogels' from methyl methacrylate or styrene and tetraoctadecylammonium bromide as gelator", Chem. Commun., pp. 543-544 1997.

Teresa Ruiz, et al., Biol. Cell, vol. 80, pp. 203-210 1994.

* cited by examiner

_US 7,381,566 B2_

METHOD FOR PREPARING ORGANIC NANOTUBULES OF LITHOCHOLIC ACID, NANOTUBULES DERIVED THEREFROM, AND USES THEREOF

RELATED APPLICATIONS

This is a U.S. national phase filing under 35 U.S.C. § 371 of PCT/FR02/02166 filed Jun. 21, 2002 and claims priority from FR 0109299 filed Jul. 12, 2001.

TECHNICAL FIELD

The object of the present invention is the manufacturing of organic nanotubules.

Such nanotubules may find various applications, notably in the sector of biosensors and carriers of active ingredients, and in the nanoelectronics sector.

STATE OF THE PRIOR ART

Spontaneous self-assembly of small molecules into nanostructures is a mild and simple alternative method for manufacturing materials, the activity center of which is also located at a nanoscopic scale. Two large application sectors may be concerned by these nanotubular structures, as described by Bong, D. T., Clark, T. D. Granja, J. R. and Ghadiri, M. R. (2001), Angew. Chem. Int. Ed., 40, 988-1011, [1].

The first sector is that of chemistry where these nanotubular structures may be used in biosensors or for transporting bioactive products.

The second sector is that of electronics and electro-optics, as described by Trau M., Yao N., Kim E., Xia Y., Whitesides, G. M. and Aksay I. A. (1997), Nature, 390, 674-676 [2].

Schematically, the functioning of applications in the first sector may be summarized by showing that the tubules may be used as such if the medium where they exist is compatible with the one to be probed or treated. Diffusion limited by the size of the hollow core of the tubule may be the operational principle of one of these types of applications. If this core may be suitably functionalized so as to exhibit electronic and/or ionic conduction properties as described by Van Nostrum, C. F. (1996), Adv. Mater., 8, 1027-1030 [3], other applications are possible.

The second field of application proceeds with the stiffening of the tubules in order to make a solid replicate which in turn may be used for the aforementioned applications, but also for manufacturing electro-active composite materials. This stiffening step may be achieved by metallization of the structures or mineralization with silica. At the same time, electromagnetic properties of interest for the applications may be introduced by metallization. Mineralization is a mild chemistry method providing a transition from the organic domain to the mineral domain, fields of application for carbon nanotubes as described by Dekker, C. (1999), Physics Today, 52, 22-28 [4] may be rediscovered with stiffened tubules as described by Schnur, J. M. (1993), Science, 262, 1669-1676 [5], and Schnur, J. M. and Shashidhar, R. (1994), Adv. Mater., 6, 971-974 [6].

As for applications outside the electronics and optoelectronics field, catalysis, biomolecular separation and the preparation of porous membranes with calibrated holes for filtration applications where a replica is made by polymerization around fibrillar structures as described by Gu, W., Lu, L. Chapman, G. B. and Weiss, R. G. (1997) J. Chem. Soc., Chem. Commun., 543-544 [7], may be also mentioned.

Other silica-based structures have been described by Jung, H. J. Amaike, M. and Shinkai S. (2000), J. Chem. Soc., Chem. Commun., 2343-2344 [8].

Very often, the effectiveness of a system formed from nanoscopic individual active components will be enhanced if these components are orientated and aligned.

Presently, chemical systems leading to the formation of tubules belong to the following chemical classes described in reference [1]:
 linear or cyclic peptides,
 macrocycles,
 cyclodextrins,
 lipids, and
 block copolymers.

With these molecules, the internal diameter of the tubules is not always in the nanometer range, between a few tens of angstroms, ($1/10^{th}$ of a nanometer, i.e. $10^{-9}$ m) and few hundreds of angstroms. Moreover, these molecules result from sometimes complex chemical syntheses.

The manufacturing methods often involve a heating step and sometimes several constituents.

Moreover, the orientation of the tubules assumes that they weakly interact with each other and then the use of electric fields is required. In other cases, orientation is achieved by using microcapillaries as described in reference [7].

Thus, in reference [2], tubules may be obtained from self-assembly of fibers full of cetyltrimethylammonium chloride. Their orientation is achieved by applying an electric field in microcapillaries where the chemical reaction for forming the tubules and simultaneous mineralization are conducted. Here, the alignment procedure is therefore complex. The internal diameter of the resulting tubule is set by the diameter of the initial full fibers; the external diameter cannot be monitored accurately. The starting product is a synthetic surfactant.

In reference [8], silica tubules are obtained via a sol-gel polymerization technique on organic structures.

In references [5] and [6], tubules may be formed from the polymerizable phospholipid, 1,2-bis(tricosa)-10,12-10-diynoyl)sn-glycero-3-phosphocholine which is not a simple chemical structure. The internal diameter is of the order of 0.2 to 0.7 µm and is not located in the nanoscopic range.

The methods and molecules used hitherto for forming tubules thus have certain drawbacks.

Indeed, they do not meet the whole set of sought-after features for obtaining such structures, which are:

1) the ease in obtaining the starting product in order to avoid complex and costly chemical syntheses;
2) the ease in obtaining tubules from the starting product;
3) the homogeneity of the formed structures, i.e., the dimensions of the external diameter and of the internal hole which must be perfectly calibrated;
4) the stability of the formed nanostructures; and
5) the ease in obtaining tubules aligned in parallel with each other.

DISCUSSION OF THE INVENTION

Specifically, the object of the present invention is a method for obtaining tubules for which the dimensions of the external diameter and of the internal diameter, i.e., of the internal hole, are perfectly calibrated in the nanometer range, by using as a starting product, a naturally secreted bile product and which does not require any further organic synthesis operation, and with which nanotubules may easily be obtained in an aqueous medium.

According to the invention, the method for preparing organic nanotubules in an aqueous medium comprises the following steps:

a) preparing a basic aqueous solution with a pH from 10 to 14, preferably from 12 to 13.5, b) adding to the solution an organic compound of formula:

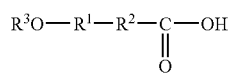

wherein $R^1$ is a $C_{17}$-$C_{20}$ polycyclic radical with fused rings, optionally including one or more $C_{17}$-$C_{20}$ alkyl substituents, $R^2$ is a $C_3$-$C_{20}$ linear or branched alkylene, and $R^3$ represents a hydrogen atom, a $C_1$-$C_{20}$ alkyl or a $C_6$-$C_{30}$ aromatic group, and c) submitting the solution to stirring for sufficient time in order to form stable tubules of the organic compound in the solution.

The starting organic compound used in the invention thus comprises a carboxyl and hydroxyl group separated by a polycyclic optionally substituted radical with fused rings and an alkylene group with which tubules of calibrated dimensions may easily be formed.

The $R^2$ group of this compound is an alkylene group which may include from 3 to 20 carbon atoms, preferably from 3 to 8 carbon atoms.

As an example of such a group, the group:

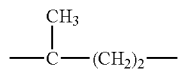

may be mentioned.

In these compounds, the $R^1$ group is a polycyclic group with fused rings, which may be derived from natural products such as steroids.

In this compound, the dimensions of the tubules, i.e., their internal and external diameters may be adjusted in particular by selecting groups $R^1$ and $R^2$.

As examples of such polycyclic groups, the group of formula:

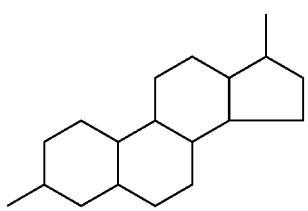

may be mentioned, which may include one or several $C_1$ to about $C_{20}$ alkyl substituents.

According to the invention, $R^3$ may represent a hydrogen atom, a $C_1$-$C_{20}$ linear or branched alkyl, or a $C_6$-$C_{30}$ aromatic group.

By aromatic group, a group is meant having one or more benzene, naphthalene, anthracene rings, and which may optionally include heteroatoms such as O, S and N.

As examples of such aromatic groups, groups derived from anthracene, benzene and naphthalene may be mentioned, such as anthryl, benzyl and naphthyl groups, and groups derived from azobenzene.

Preferably, according to the invention, the starting organic compound is lithocholic acid of formula:

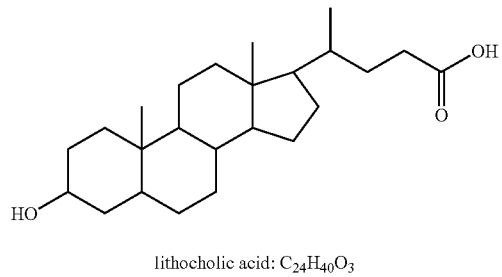

lithocholic acid: $C_{24}H_{40}O_3$

According to the invention, this acid which is normally insoluble in water at a neutral or acid pH, is solubilized as stable nanotubules by using a basic medium with a suitably adjusted pH. By simply stirring the medium, nanotubules with monodispersed dimensions are obtained and are a signature of the initial constituent. The tubules may be orientated by simple shearing of the solution.

Thus, the method of the invention does not require any heating, and uses a natural starting product which does not require any further organic synthesis operation; it further does not require the use of electrical fields or micro-etchings for orientating the tubules; it therefore meets the whole set of sought-after features for obtaining the tubules.

According to the invention, the aqueous medium is a basic medium, preferably with a pH from 12 to 13.5. An aqueous sodium hydroxide solution may be used. When the starting compound is lithocholic acid, a sodium hydroxide solution is preferably used with a pH of about 12.5.

Adjustment of the pH of this medium, as well as the nature of the base used (ionic force, counter-ions), and the concentration of organic compounds, are also a means for adjusting the amplitude of the interactions between tubules.

Preferably, this organic compound concentration is from 0.01% to 20% by weight.

According to the invention, the kind of polycyclic radical $R^1$ and the aqueous medium (light water, heavy water) also play a role on the structural features of the tubules.

The object of the invention is further the use of organic nanotubules obtained by this method for manufacturing inorganic nanotubes by mineralization, for manufacturing field emission cathodes by metallization of nanotubes or furthermore for manufacturing biosensors.

Other features and advantages of the invention will become more apparent upon reading the following description, naturally given as illustrative and non-limiting, with reference to the appended drawings.

DETAILED DISCUSSION OF AN EMBODIMENT

An example of the preparation of lithocholic acid tubules is described hereafter.

First of all, a basic aqueous solution is prepared with a pH of about 12.5, by adding 0.125 g of sodium hydroxide to 100 g of water. Next, 0.3 grams of lithocholic acid are added to the obtained solution. The whole solution is submitted to stirring by means of a magnetic stirrer for about half an hour and a solution of tubules at a concentration of 0.3% by weight is thereby obtained.

The structure of the tubules is characterized by the complementary use of central X-ray and neutron scattering (reciprocal space of the wavenumber transfer moment) and by transmission electron microscopy (real space with three spatial dimensions).

Central X-ray scattering has the advantage of irradiating a large sample volume, and of thus obtaining a response which is a statistical average of the probed nanostructures on this volume. The response is a curve of the scattered intensity versus the scattering angle which has up to seven characteristic oscillations and a characteristic decay.

These components may be accounted for with theoretical modeling, if a geometrical model of hollow tubes with an external diameter of 520 angstroms and with an internal diameter of 490 angstroms is used.

Figure 1:
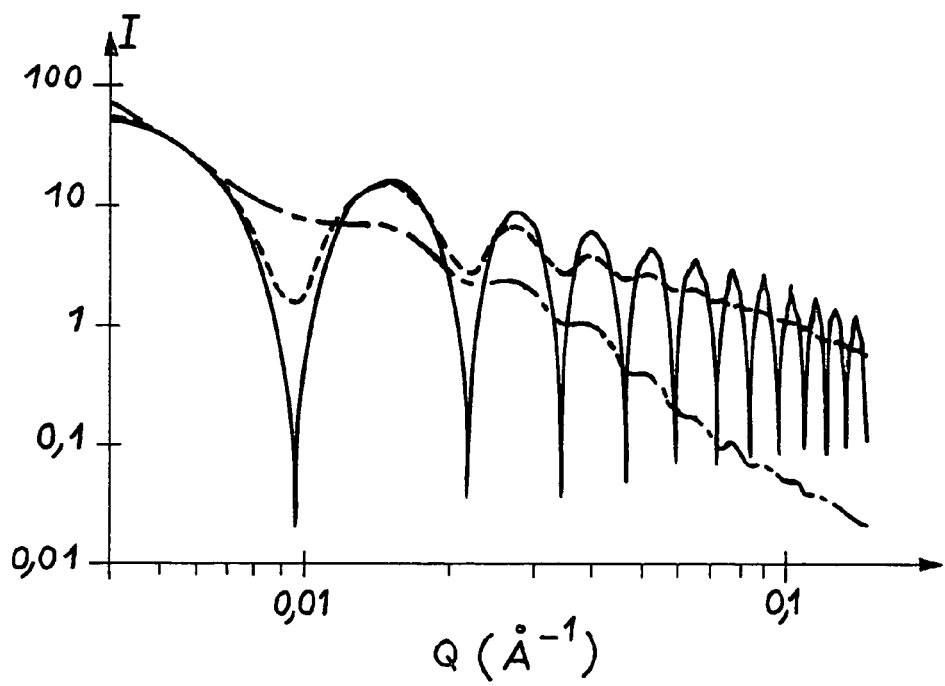
FIG. 1 illustrates typical X-ray scattering from a system of lithocholic acid tubules in a basic medium.

FIG. 1 illustrates typical X-ray scattering from a system of tubules (scattered intensity versus scattering angle).

In this figure, several experimental oscillations (curve with dot and dash lines) are seen, which the simplified theoretical model of a hollow cylinder (curves in solid lines and dashed lines) reproduces in their positions.

Unambiguous confirmation of the existence of these tubules is brought by transmission electron microscope photographs. The apparatus and experimental procedure used are selected for direct observation of the structures without any manipulation of the system. The electronic contrast of the system deposited as a very thin layer (about 3,000 angstroms) is utilized on a cooled stage of a specialized microscope. This method is described by T. Ruiz, I. Erk and J. Lepault in Biol. Cell, 1994, 80, p 203-210 [9], for observing brittle biological structures.

Figure 2:
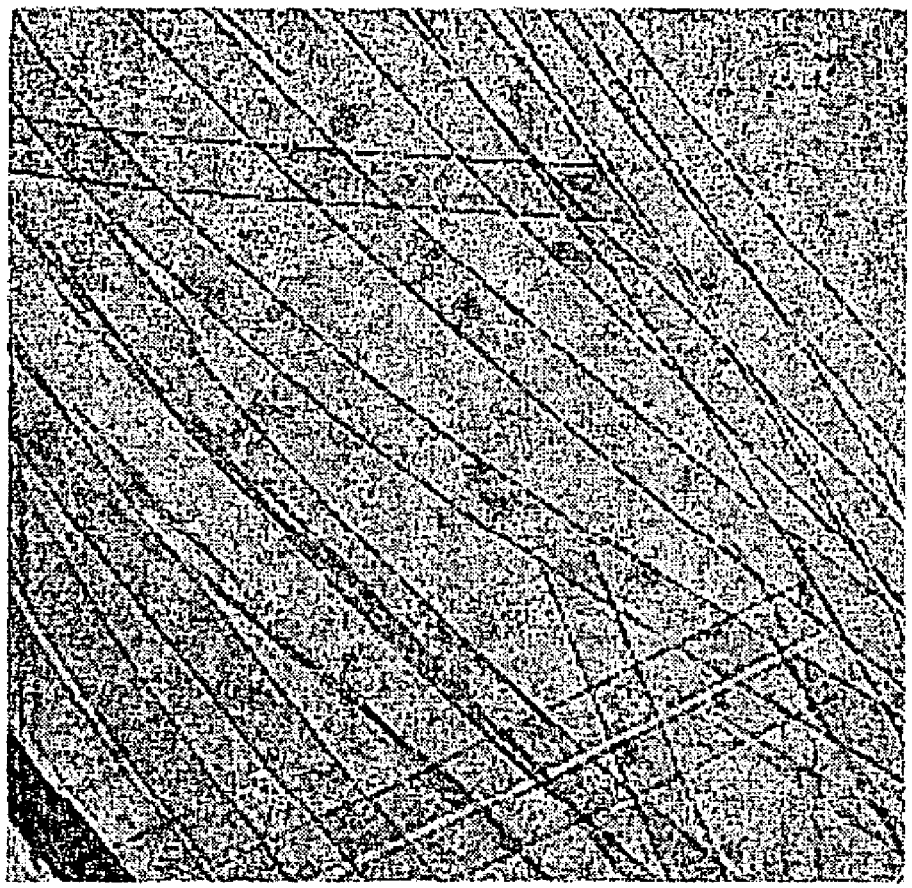
FIG. 2 is an electron micrograph of lithocholic acid tubules.

FIG. 2 is an electron micrograph showing the quasi-exclusive presence of long hollow cylinders. The walls and ends of these tubules may perfectly be seen in this figure. The external and internal diameters are 520 angstroms and 490 angstroms respectively.

The possibilities of orientation of the tubules are now examined in the case of the 0.3% tubule solution and in the case of a solution of tubules at a concentration of 2.4% obtained in the same way.

For this purpose, the aqueous solution containing the tubules is submitted to a shear or elongational stress ($\gamma$) in order to orientate the tubules.

The value of this minimum shear stress is small, typically of about 100 $s^{-1}$ for a concentration of about 2%. Superior results are obtained from stretched fibers (elongation) of a more concentrated highly viscous solution (7%). Characterization is performed by central X-ray scattering.

For this purpose, a sample of tubules is placed in the 1 mm gap formed by two coaxial cylinders, with the rotation of the external element generating a shear in the gap. The gap is struck by an X-ray beam, whereby the scattered intensity thereof by a two-dimensional detector enables the degree of orientation of the tubules to be analyzed. If the tubules are randomly distributed in the sample's volume, the scattering signal becomes apparent on the detector 2d by iso-intensity lines which are circular. In this rest configuration, the scattering signature is then re-discovered with the aforementioned characteristic oscillations.

When the sample is stretched, the positions of the tubules become correlated and the scattering signal is more or less strongly deformed according to the degree of orientation. Thus, one passes from circular iso-intensity lines to elliptical lines then to a line joining the scattering spots, this is what is observed with the alkaline tubule solution.

The orientability may also be apprehended or monitored by more traditional viscoelasticity measurements.

In this case, regardless of the concentration used, the level of mutual interactions of the tubules is measured, i.e., the stress vs. shear rate curves and the changes in viscosity when the shear rate increases. Under these conditions, fluidification of the system is observed due to these orientation effects. These measurements may be carried out with a simple rheometer.

The nanotubules may be identified by their dimensions (external, internal diameters and thickness of the wall) and their physico-chemical characteristics, in particular the parameters describing their viscoelasticity (flow curves, threshold stresses, elasticity and viscosity).

Figure 3:
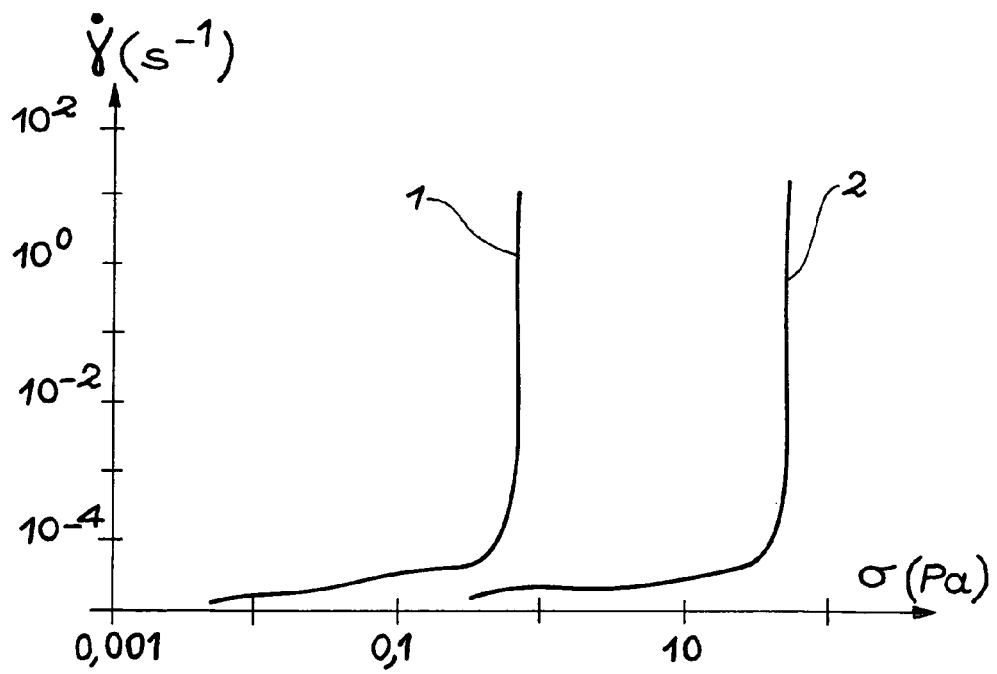
FIG. 3 illustrates the curves of stress σ (in Pa) versus shear rate $\dot{\gamma}$ or $d\gamma/dt$ (in $s^{-1}$) for two solutions of lithocholic acid tubules.

FIG. 3 depicts an example of a rheological imprint of the system and illustrates the stress vs. shear rate curves, for two tubule solutions with a concentration of 0.3% (curve 1) and a concentration of 2.4% (curve 2). The threshold stresses ($\sigma 1$ and $\sigma 2$) of both solutions are thereby obtained. The transverse dimensions of the tubules and their rheological features are set by the chemical formula of the constituent, lithocholic acid, and of the type of liquid used.

CITED REFERENCES

[1] Bong, D. T., Clark, T. D. Granja, J. R. and Ghadiri, M. R. (2001), Angew. Chem. Int. Ed., 40, 988-1011.

[2] Trau M., Yao N., Kim E., Xia Y., Whitesides, G. M. and Aksay I. A. (1997), Nature, 390, 674-676.

[3] Van Nostrum, C. F. (1996), Adv. Mater., 8, 1027-1030.

[4] Dekker, C. (1999), Physics Today, 52, 22-28.

[5] Schnur, J. M. (1993), Science, 262, 1669-1676.

[6] Schnur, J. M. and Shashidhar, R. (1994), Adv. Mater., 6, 971-974.

[7] Gu, W., Lu, L., Chapman, G. B. and Weiss, R. G. (1997) J. Chem. Soc., Chem. Commun., 543-544.

[8] Jung, H. J., Amaike, M. and Shinkai, S. (2000), J. Chem. Soc., Chem. Commun., 2343-2344.

[9] Ruiz et al. in Biol. Cell, 1994, 80, 203-210.

What is claimed is:

1. A method for preparing nanotubules consisting of lithocholic acid in an aqueous medium, comprising the following steps:
    a) preparing a basic aqueous solution with a pH from 12 to 14,
    b) adding lithocholic acid to the basic aqueous solution, wherein the lithocholic acid is of formula:

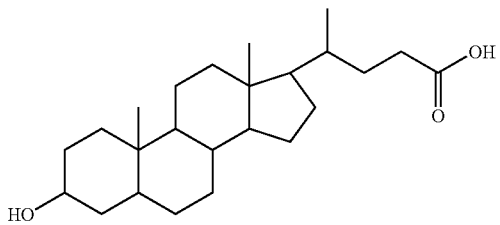

and c) stirring the basic aqueous solution containing the lithocholic acid to form stable nanotubules consisting of lithocholic acid in the basic aqueous solution.

2. The method according to claim 1, wherein the basic aqueous solution is a sodium hydroxide solution.

3. The method according to claim 1, wherein the basic aqueous solution is a sodium hydroxide solution with a pH of about 12.5.

4. An aqueous medium comprising nanotubules consisting of lithocholic acid of formula:

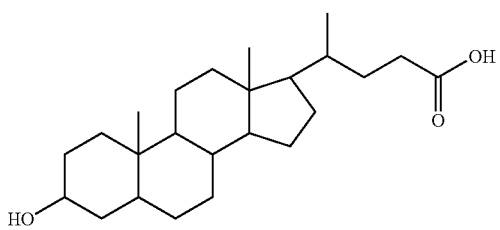

wherein the nanotubule is in the form of a nanoscopic hollow cylinder having an internal hole in the nanometer range, wherein the aqueous medium has a pH of from 12-14.

5. The method according to claim 1, wherein the basic aqueous solution prepared in step a) has a pH from 12 to 13.5.

6. The method according to claim 1, wherein the nanotubules are nanoscopic long hollow cylinders having an internal hole in the nanometer range.

7. The method according to claim 1, wherein the nanotubules have an internal diameter of from 0.1 nanometer to 1 nanometer.

8. The method aqueous medium according to claim 4, wherein the nanotubule has an internal diameter of from 0.1 nanometer to 1 nanometer.

9. The aqueous medium according to claim 4, wherein the nanotubules consisting of lithocholic acid are obtained by:

i. preparing a basic solution having pH of from 12 to 14, ii. adding lithocholic acid to the basic solution, wherein the lithocholic acid is of formula:

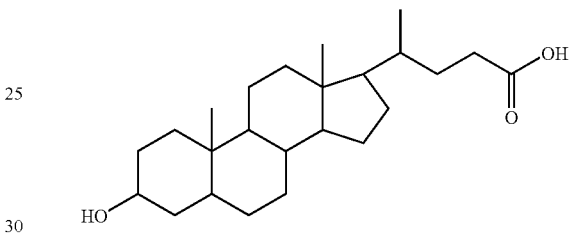

and iii. stirring the basic aqueous solution containing the lithocholic acid to form stable nanotubules consisting of lithocholic acid in the basic aqueous solution.

* * * * *